(12) United States Patent
Wakita et al.

(10) Patent No.: US 7,369,218 B2
(45) Date of Patent: May 6, 2008

(54) ANALYSIS DISC WITH ANALYSIS OBJECT

(75) Inventors: Tsugio Wakita, Matsuyama (JP); Mitsuteru Fujimoto, Saijo (JP); Satoshi Miyagawa, Niihama (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 11/892,468

(22) Filed: Aug. 23, 2007

(65) Prior Publication Data

US 2008/0007721 A1    Jan. 10, 2008

Related U.S. Application Data

(62) Division of application No. 10/507,412, filed as application No. PCT/JP03/02806 on Mar. 10, 2003.

(30) Foreign Application Priority Data

Mar. 14, 2002   (JP) .............................. 2002-069375

(51) Int. Cl.
   *G01N 33/48*   (2006.01)
(52) U.S. Cl. ........................................ 356/39; 356/244
(58) Field of Classification Search .................. 356/39, 356/244
   See application file for complete search history.

(56) References Cited

U.S. PATENT DOCUMENTS 5,922,617 A  *  7/1999  Wang et al. ................. 436/518

6,582,662 B1  *  6/2003  Kellogg et al. ................ 422/72
2003/0224457 A1  *  12/2003  Hurt et al. .................... 435/7.2

FOREIGN PATENT DOCUMENTS

| JP | 3-225278 | 10/1991 |
|---|---|---|
| JP | 2001-522998 | 11/1991 |
| JP | 2001-238674 | 9/2001 |
| WO | WO 96/095548 | 3/1996 |
| WO | WO 99/09394 | 2/1999 |
| WO | WO 99/24822 | 5/1999 |
| WO | WO 02/16037 | 2/2002 |
| WO | WO 02/056311 | 7/2002 |
| WO | WO 02/093167 | 11/2002 |

* cited by examiner

*Primary Examiner*—Roy M Punnoose
(74) *Attorney, Agent, or Firm*—Steptoe & Johnson LLP (57) ABSTRACT

An analysis apparatus capable of normally creating image data and an analysis disc used for this. Instead of using a signal which has been read in time series by pickup following a track so as to create an image by utilizing address information engraved on an optical disc, a mark (110) is recorded over the radius direction (A) of a read area (109) of the analysis disc (108) where an analysis object (B) is arranged, at least at a preceding position or a following position of the read area (109) in the rotation direction (C), so that video processing aligned according to this mark is executed, thereby executing video acquisition or a shape count with a high accuracy.

5 Claims, 11 Drawing Sheets

ANALYSIS DISC WITH ANALYSIS OBJECT

This is a Divisional Application of Ser. No. 10/507,412, filed Sep. 13, 2004, which claims Priority to Japanese Patent Application No. 2002-069375, filed Mar. 14, 2002.

TECHNICAL FIELD

The present invention relates to an analysis apparatus in which a sample like blood, for example, is set on an optical disc for analysis and such analysis object is traced and captured as an image.

BACKGROUND ART

An analysis apparatus is disclosed in Published Japanese translation of PCT international publication for patent application No. 10-504397 (WO96/09548) and so on, in which an analysis object set on the tracks of an analysis disc is traced and an image is obtained by using a compact disc for recording audio or video (hereinafter referred to as an optical disc) and the reproducing function of an optical disc drive for reproducing the disc.

Figure 9:
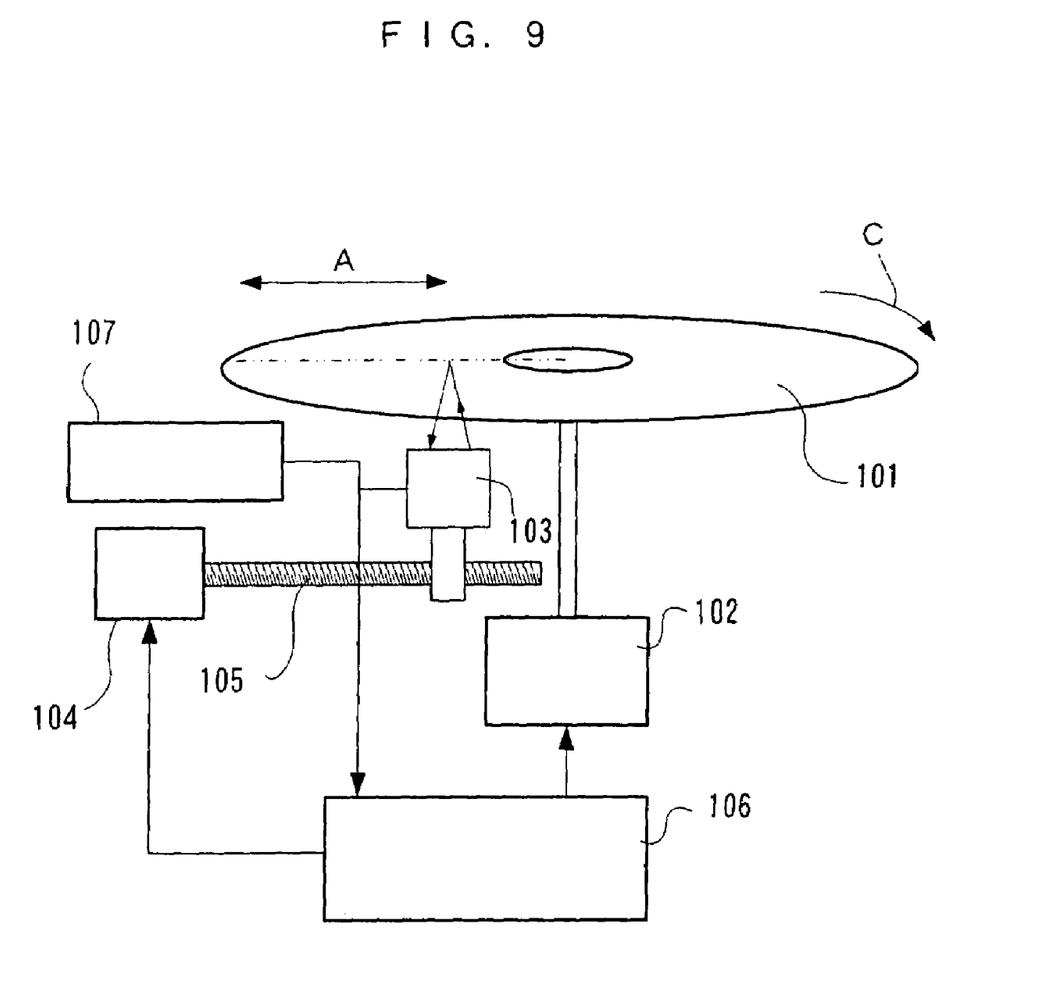
FIG. 9 is a structural diagram showing a conventional and typical optical disc drive.

To be specific, a typical optical disc drive is configured as shown in FIG. 9.

An optical disc 101 is rotationally driven in the direction of arrow C by a disc motor 102. A screw shaft 105 is rotationally driven by a traverse motor 104 so that a pickup 103 for irradiating the optical disc 101 with detection light and detecting reflected light moves in the radial direction (the direction of arrow A) of the optical disc 101.

The traverse motor 104 and the disc motor 102 are operated by a servo control circuit 106 according to the reproduction output of the pickup 103 in the following manner:

According to the reproduction output of the pickup 103, the servo control circuit 106 drives the traverse motor 104 so as to trace tracks composed of pits or grooves, etc., detects address information recorded on the tracks of the optical disc 101, and drives the disc motor 102 with a constant linear velocity (CLV control).

Further, the reproduction output of the pickup 103 is processed by a reproducing device 107, so that a sound signal or a video signal that serve as data recorded on the tracks are reproduced and outputted.

Figure 10:
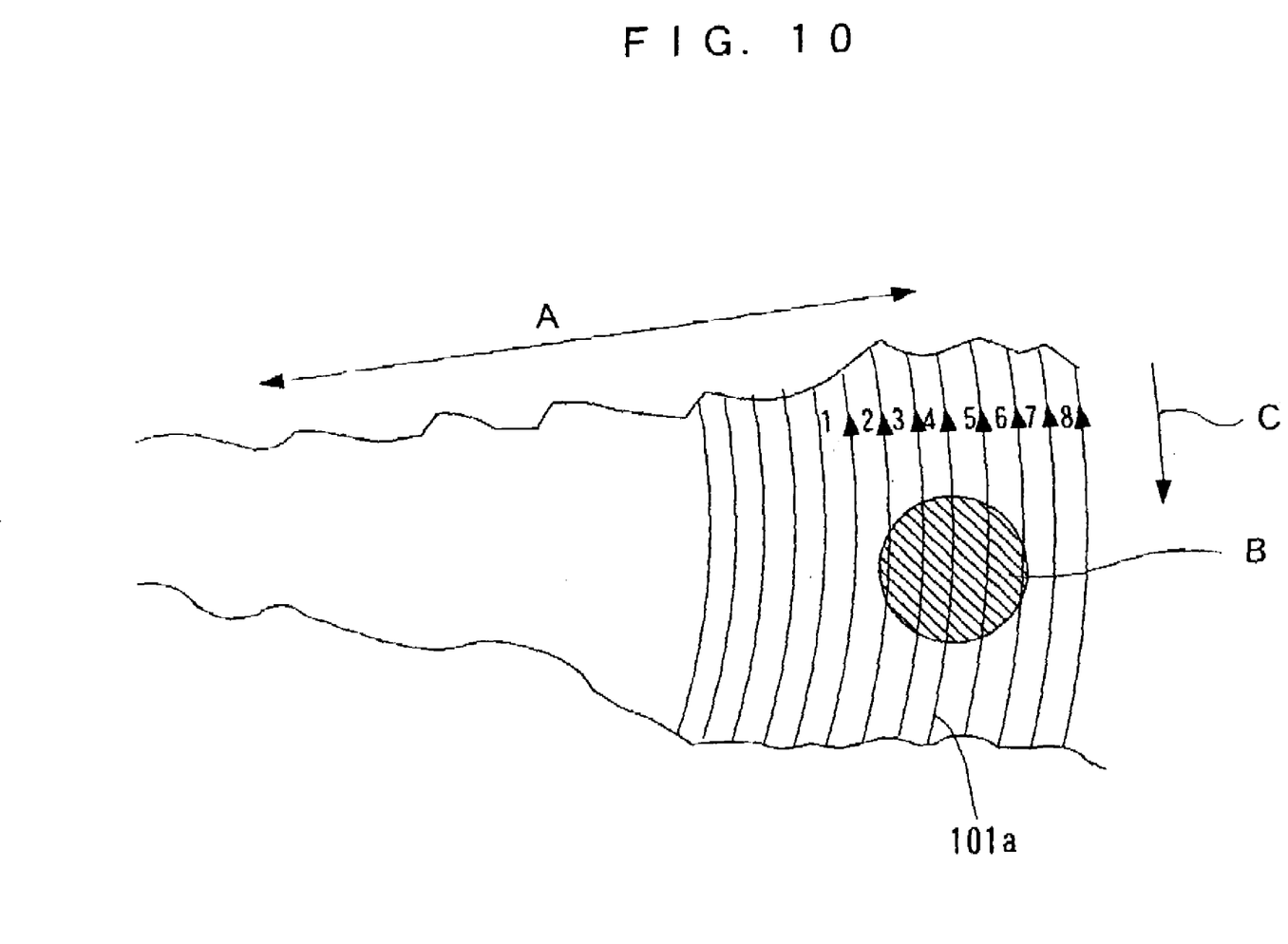
FIG. 10 is an enlarged plan view showing a main part of a conventional analysis disc.

On the other hand, the analysis apparatus is almost identical to the typical optical disc drive in block diagram form. In the case of the analysis apparatus, as shown in FIG. 10, a mixture of a sample and a reagent corresponding to a test item is set on the optical disc 101 as an analysis object B in addition to a track 101a. In the case of the analysis apparatus, the servo control circuit 106 and the reproducing device 107 obtain an image of the analysis object B on the optical disc 101 as described below. The direction of an arrow on the track 101a indicates the tracing direction of detection light from the pickup 103.

Also in the case of an analysis disc, time information or the like composed of pits, grooves, etc. on the optical disc is formed according to the standards of conventional optical discs for recording audio or video, and thus the specific explanation thereof is omitted. Specific examples are Compact Disc System Description (commonly called Red Book standard) and Compact Disc Readable System Description (commonly called Orange Book standard).

The laser irradiation point of the pickup 103 controlled by the servo control circuit 106 traces the spiral tracks 101a of the optical disc 101. The tracks 101a have a pitch of 1.6 μm on the optical disc according to Orange Book standard. The pickup 103 traces 1, 2, 3, ..., 8, ..., in turn for each rotation of the optical disc 101.

That is, in the operations of the analysis apparatus, a portion of the analysis object B and a portion of the track 101a are alternately passed and traced. In the case of the analysis apparatus, the reproducing device 107 extracts only data of a portion of the analysis object B that is obtained by tracing, and reconfigures data, so that video or shape count is performed.

The analysis apparatus may detect and process light reflected from an optical disc in the same manner as a typical optical disc drive for reproducing an optical disc, and the analysis apparatus may detect and process light passing through an optical disc.

Absolute time is engraved as address information on a disc such as a CD and a DVD. The time information is composed of minutes, seconds, and frames. One second is constituted of 75 frames.

The recording system of the time information is broadly divided into the following two kinds: a system for recording data by changing a length of a pit such as EFM and a system for recording after a groove is snaked by FM modulation on a recording disc.

Even when the ordinary time information of the optical disc is used to construct a video signal or perform shape count in the analysis apparatus, analysis accuracy cannot be expected to improve for the following reasons:

In both of the optical disc drive and the analysis apparatus, existing address information recorded on an optical disc is used to search for a given position on the optical disc 101. However, when a minimum unit distance obtained from the address information is calculated based on the example of the typical optical disc having 75 frames per second, just 120 (cm)÷75 (frames)=1.6 (cm/frame) is obtained at the minimum because the disc has a linear velocity of 1.2 to 1.5 m/S. That is, accuracy only to 16 mm can be specified even in one frame serving as the minimum unit.

An analysis apparatus for a blood test requires accuracy enabling the detection of an object of about 10 μm in a small area of 5 square millimeters on the optical disc 101. However, when video processing is performed on an image of the analysis object B, which is read in time series by the pickup 103 tracing the tracks, to obtain an accurately read image shown in FIG. 11(b), only a read image shown in FIG. 11(a) can be obtained in the present state where the reproducing device 107 performs video processing according to the address information.

Figure 11A:
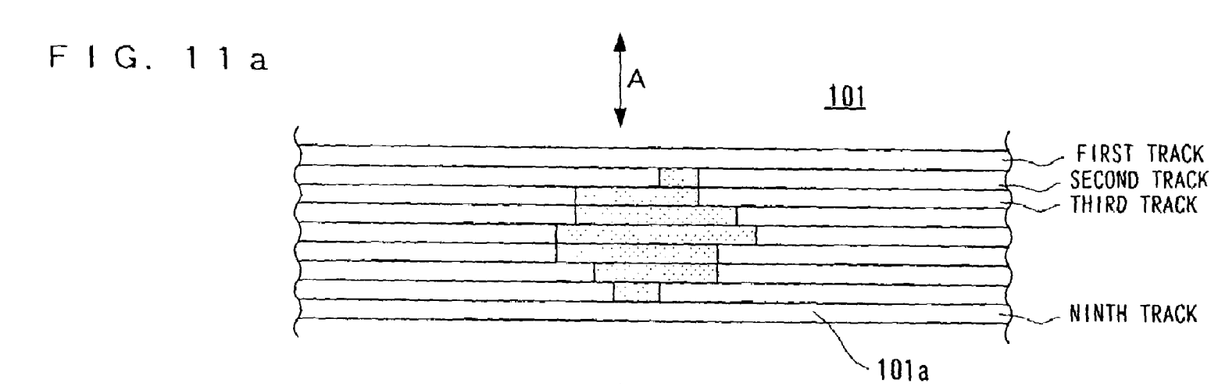
FIG. 11 is an explanatory drawing showing image processing of a conventional analysis apparatus.
Figure 11B:
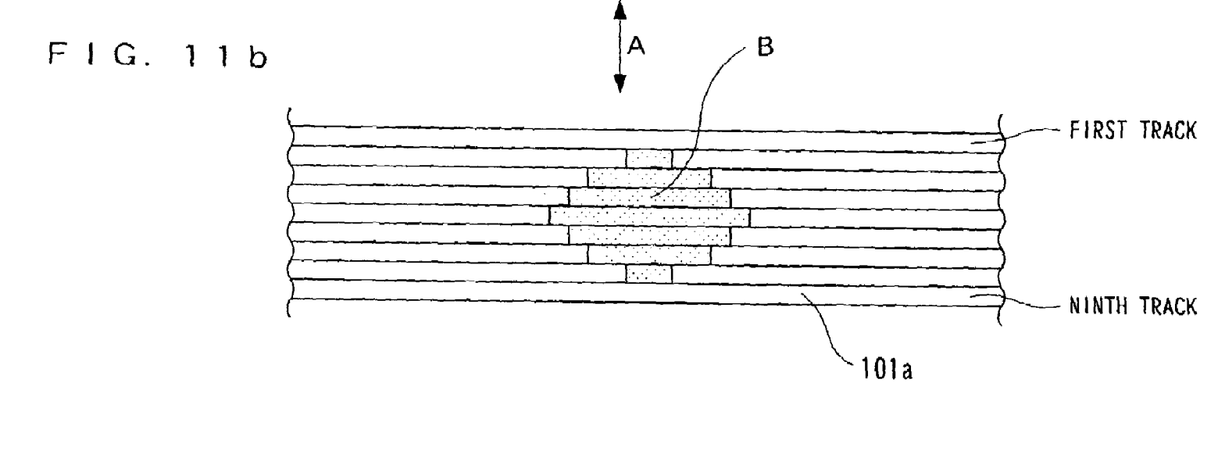

To be specific, the reproduced image has a displacement in the rotation direction C of the optical disc 101 as shown in FIG. 11(a) and has a value far from accuracy required for analysis of blood and so on. Thus, it is understood that the image is too rough to be used.

An object of the present invention is to provide an analysis apparatus which can perform shape analysis satisfying accuracy required for analysis of blood and soon, and a special analysis disc used for the same.

DISCLOSURE OF THE INVENTION

In the present invention, address information engraved on an optical disc is not used for constructing signals as an image, the signals being read in time series by a pickup which traces tracks. Video processing for alignment is performed relative to another instead of the address information, so that video acquisition or shape count is performed with high accuracy.

An analysis apparatus according to Embodiment 1 of the present invention irradiates detection light on an analysis disc having an analysis object disposed on a art thereof, and reads a state of the analysis object. The analysis disc having a mark is set in the apparatus, the mark being recorded over a radial direction of a reading area at least in one of frontward and rearward positions of the reading area in a rotation direction, and the reading area being disposed with the analysis object. The analysis apparatus comprises a pickup for detecting the mark and detection light from the analysis object disposed on the set analysis disc, and an image processor which performs video acquisition or shape count on the analysis object by performing video processing for aligning the analysis object and a reading signal of the mark by a time axis relative to a position of the mark, the analysis object and the reading signal of the mark being read in time series by the pickup that traces tracks.

The analysis disc of the present invention enables reproduction and tracing on a pit or a groove and has a data region for controlling the rotation of the disc and a reading area having an analysis object therein, wherein a mark is recorded over the radial direction of the reading area in which the analysis object is disposed, at least in one of frontward and rearward positions of the reading area in the rotation direction.

Further, according to the analysis disc of the present invention, the mark is formed as a pit, a groove, or a land, or by printing, removing a mirror surface, or forming an odd shape.

Moreover, according to the analysis disc of the present invention, the mark is formed as a pit, a groove, or a land with a specific pattern different from the data region.

Besides, according to the analysis disc of the present invention, the specific pattern of the mark is varied according to a plurality of reading areas each being disposed with the analysis object.

Further, according to the analysis disc of the present invention, the specific pattern of the mark is varied according to a kind of the analysis object disposed in the reading area.

An analysis apparatus according to Embodiment 2 of the present invention has an analysis disc having marks with different specific patterns according to a plurality of reading areas in at least one of frontward and rearward positions of the reading areas in the rotation direction, each reading area being disposed with an analysis object. The analysis apparatus comprises a pickup for detecting a mark and detection light from the analysis object disposed on the set analysis disc, and an image processor which performs video acquisition or shape count on the analysis object by performing video processing for aligning the analysis object and a reading signal of the mark by a time axis relative to the position of the mark, analysis object and the reading signal of the mark being read in time series by the pickup that traces a track. The image processor also manages video processing results according to the specific pattern in association with the reading area.

Further, an analysis apparatus according to Embodiment 3 of the present invention has marks of different specific patterns according to a kind of an analysis object, in at least one of frontward and rearward position of a reading area in the rotation direction, the reading area on a set analysis disc being disposed with the analysis object. The analysis apparatus comprises a pickup for detecting the mark and detection light from the analysis object, and an image processor which performs video acquisition or shape count on the analysis object by performing video processing for aligning the analysis object and a reading signal of the mark by a time axis relative to the position of the mark, the analysis object and the reading signals of the mark being read in time series by the pickup that traces a track. The image processor also manages video processing results according to the specific pattern in association with the kind of the analysis object disposed in the reading area.

BEST MODE FOR CARRYING OUT THE INVENTION

Referring to FIGS. 1 to 8, embodiments of the present invention will be described below.

Embodiment 1

Figure 1:
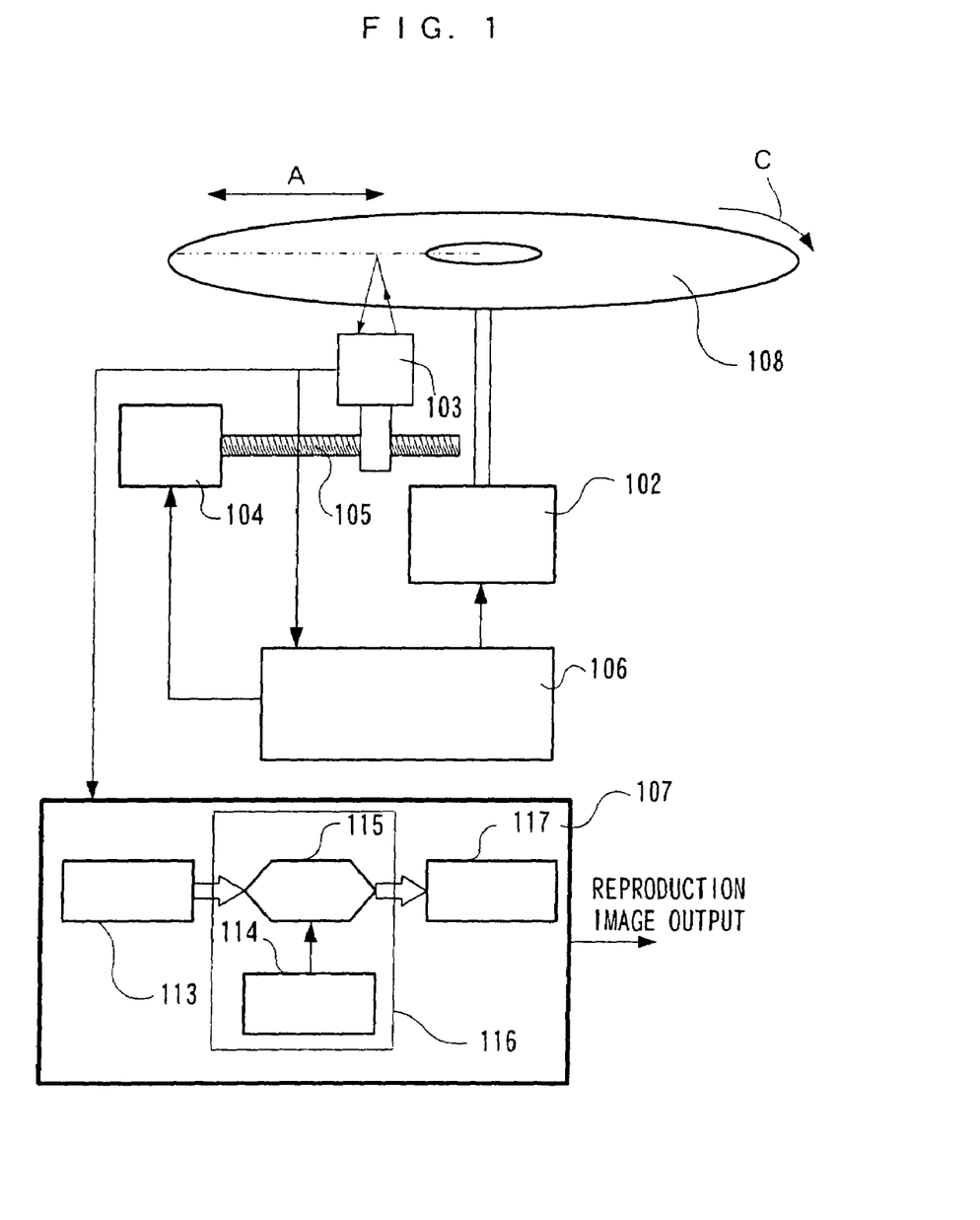
FIG. 1 is a structural diagram showing an analysis apparatus according to Embodiment 1 of the present invention.

FIG. 1 shows an analysis apparatus of the present invention. The configuration of a reproducing device 107 constituted of a microcomputer and an analysis disc 108 used for analysis instead of the optical disc 101 are different from those of the conventional art.

Figure 2:
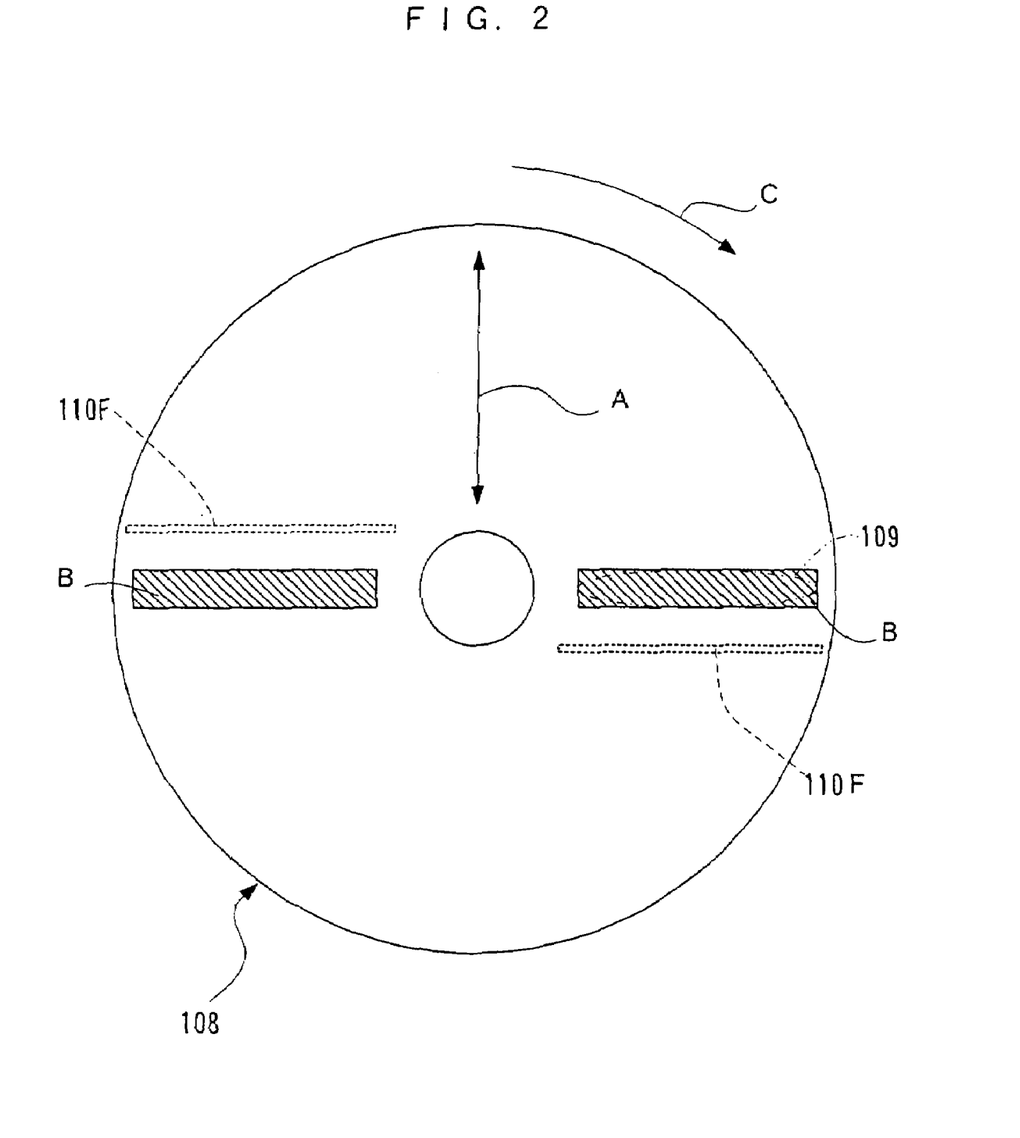
FIG. 2 is a plan view showing an analysis disc used for the embodiment.
Figure 3:
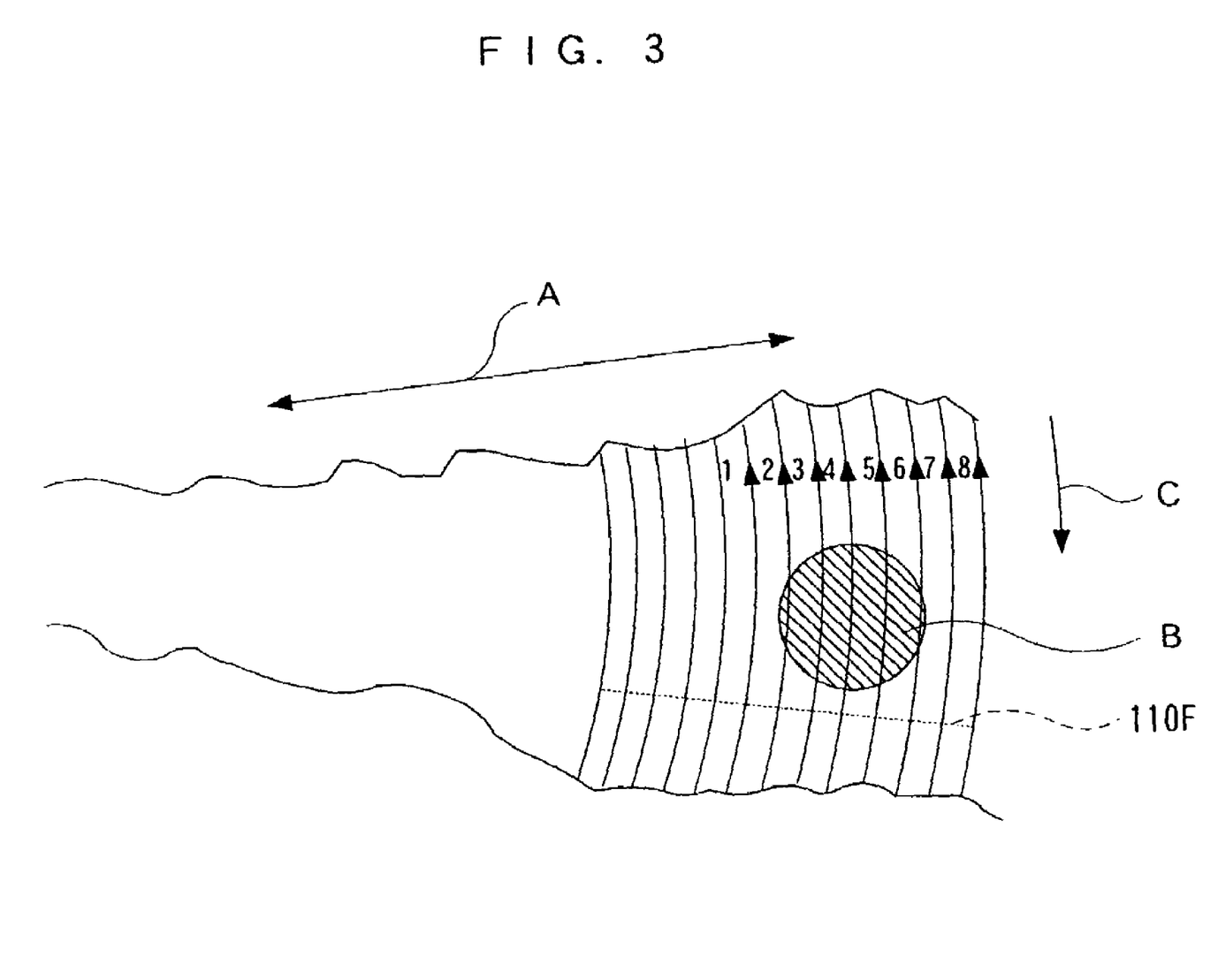
FIG. 3 is an enlarged plan view showing a main part of the analysis disc according to the embodiment.

As shown in FIG. 2, the analysis disc 108 is configured so that a mixture of a sample and a reagent corresponding to a test item is set as an analysis object B on the optical disc 101. Only on a position immediately in front of a reading area 109 in a rotation direction C, the reading area 109 having the analysis object B therein, a mark 110F is recorded over the radial direction (the direction of arrow A) of the reading area. In FIG. 2, two analysis objects B are provided on the analysis disc 108 and the marks 110F are formed immediately in front of the analysis objects B.

Figure 5A:
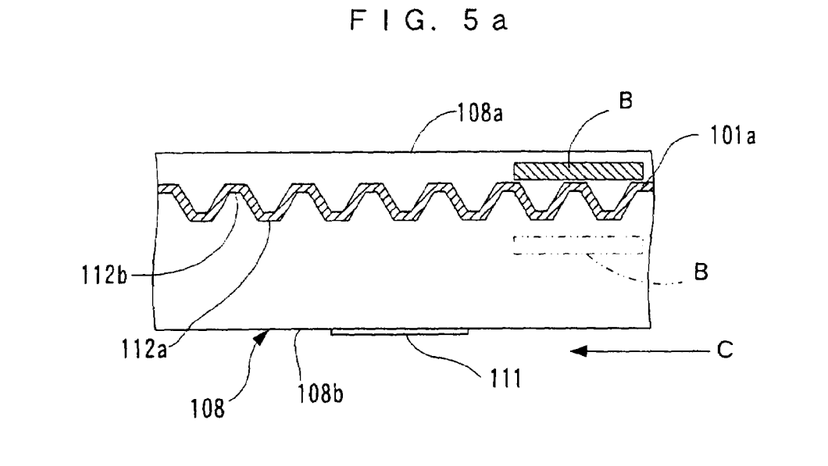
FIG. 5 is an enlarged sectional view showing the formation of a mark, taken along the track of the analysis disc according to each embodiment.
Figure 5B:
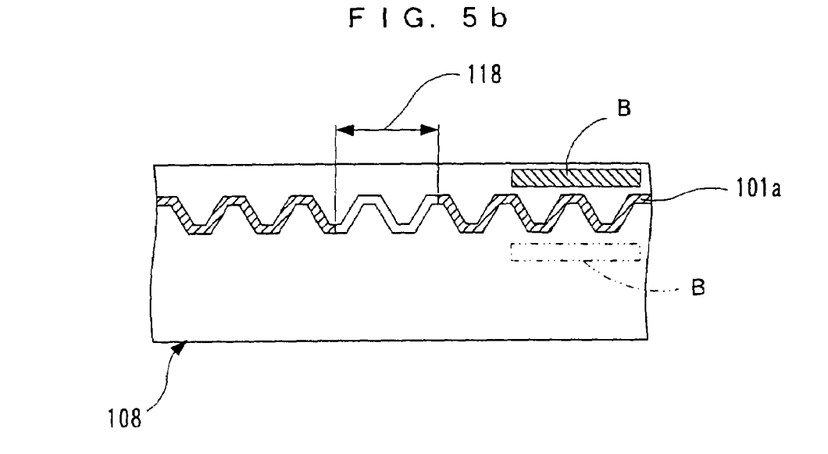
Figure 5C:
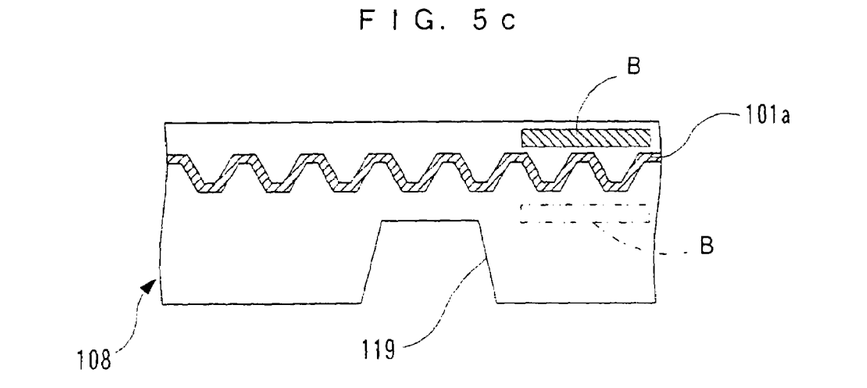

FIG. 5 shows specific examples of the position of the analysis object B in the analysis disc 108 and the mark 110F in the analysis disc 108.

As shown in FIG. 5(a), the analysis object B is provided between a surface 108a and a track 101a of the analysis disc 108. The mark 110F is formed by printing ink 111 like a belt on the back of the optical disc 101. In FIG. 5(a), reference numeral 112a denotes a pit or a groove formed on the track 101a which has been subjected to mirror-like finishing.

Reference numeral 112b denotes a land formed on the track 101a which has been subjected to mirror-like finishing.

As indicated by a virtual line of FIG. 5(a), the analysis object B may be provided between the track 101a and a back 108b of the analysis disc 108.

A pickup 103 traces the spiral track 101a of the analysis disc 108. A servo control circuit 106 drives a traverse motor 104 so that the track 101a composed of pits or grooves and so on is traced according to the reproduction output of the pickup 103. Further, the servo control circuit 106 detects the address information recorded on the track 101a and drives a disc motor 102 with a constant linear velocity (CLV control).

The reproducing device 107 serving as an image processor is configured as below.

The reproducing device 107 first accumulates image data, which has been read by the pickup 103 in time series, as trace data in a memory 113. In this case, similar processing is performed on the two analysis objects B. Thus, referring to FIG. 5, one of the analysis objects B will be discussed as an example to describe the contents of the processing.

Figure 4A:
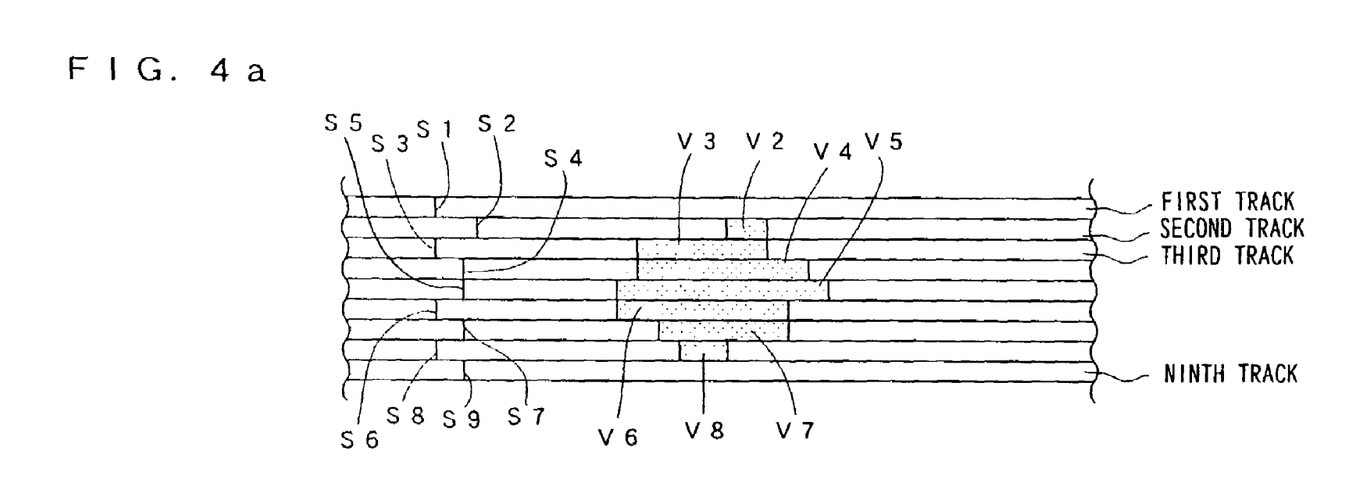
FIG. 4 is an explanatory drawing showing image processing of the analysis apparatus according to the embodiment.
Figure 4B:
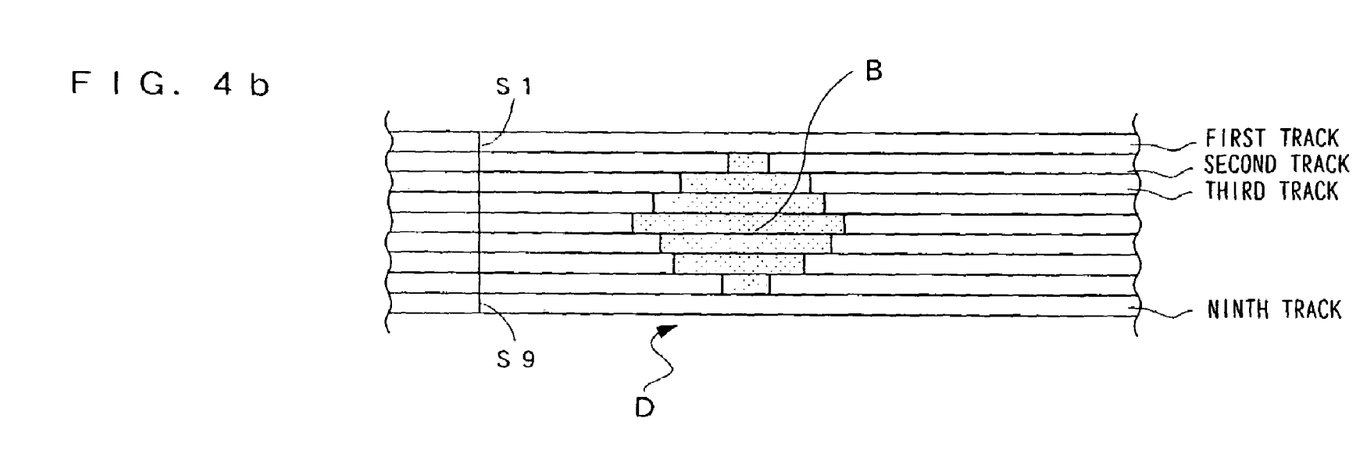

FIG. 4(a) shows trace data. The pickup 103 traces first to ninth tracks in this order from above to below in FIG. 4(a) for each rotation of the optical disc 101, and accumulates the trace data in the memory 113. In this case, a part of the analysis object B is positioned on the second track to the eighth track. Reference numerals V2 to V8 represent the resolution image data of the analysis object B. Reference numerals S1 to S9 represent trigger signals on respective track positions where the mark 110F has been read.

A first processing section 116 is constituted of a trigger circuit 114 for detecting a trigger signal in trace data having been read from the memory 113 and a switch circuit 115 for correcting the time axis of trace data in each track based on the detection output of the trigger circuit 114. The first processing section 116 properly delays the timing to output the trace data, which has been read from the memory 113, to the subsequent stage, moves the time axis of trace data in each track so that the positions of the trigger signals S1 to S9 are aligned with one another as show in FIG. 4(b), and outputs image data D. To be specific, in FIG. 4, the outputs of the trigger signals S1 and S3 to S9 are delayed so as to be aligned with the position of the trigger signal S2.

The trace data in each track that has been subjected to time base correction relative to the mark 110F is accumulated in a second processing section 117. Then, the trace data is outputted as reproduction image output. Further, when shape count is necessary as well as video acquisition of the analysis object, counting is performed in each unit area.

In this way, the time axes are aligned relative to the position of the mark 110F, so that image data can be obtained with higher accuracy than the conventional art, in which time axes are aligned relative to address information.

Embodiment 2

Figure 6:
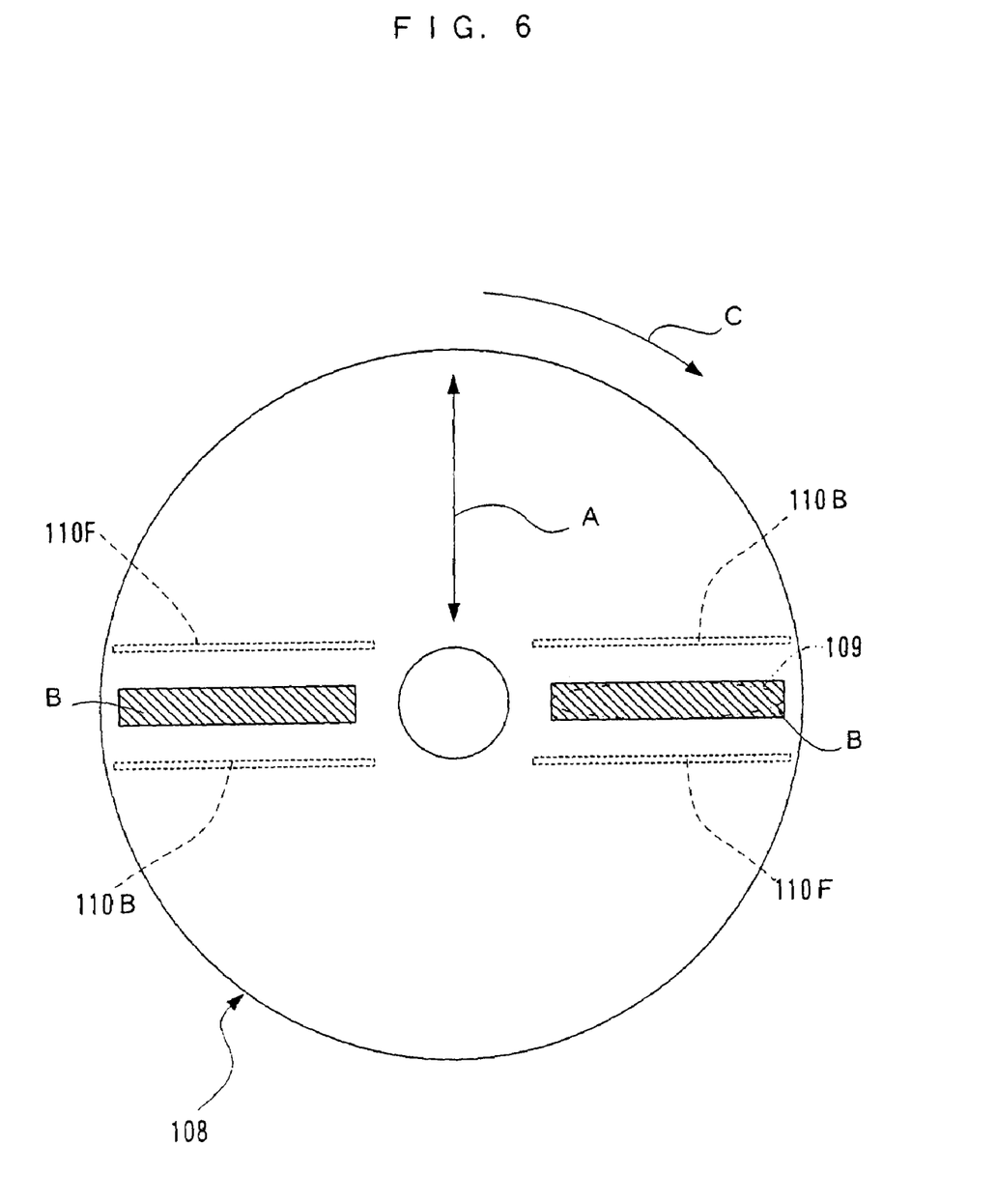
FIG. 6 is a plan view showing an analysis disc according to Embodiment 2 of the present invention.

FIG. 6 shows an analysis disc of Embodiment 2.

In Embodiment 1, the mark 110F is disposed only on a position immediately in front of the reading area 109 in the rotating direction C, the reading area 109 having the analysis object B therein. On an analysis disc 108 shown in FIG. 6, a mark 110B identical to the mark 110F is disposed just behind an analysis object B.

In the case of Embodiment 1 where the mark 110B is not provided, trace data of one track is recorded in the first memory 113 until the subsequent mark 110F is read. In the case where the analysis disc having the mark 110F just behind the analysis object B is used and a reproducing device 107 of the analysis apparatus accumulates trace data in the first memory 113 from when the mark 110F is read until the mark 110B is read, it is possible to prevent accumulation and processing from being performed on trace data in a part irrelevant to the analysis object B. Thus, efficient data processing can be expected.

Embodiment 3

In Embodiment 1, the reproducing device 107 of the analysis apparatus performs time base correction so that the trigger signals S1 to S9 having read the mark 110F are aligned with one another. The same effect as Embodiment 1 can be expected also by using an analysis disc 108 where the mark 110F is absent and the mark 110B is provided just behind the analysis object B, and a reproducing device 107 of the analysis apparatus performs time base correction so that trigger signals having read the mark 110B are aligned with one another.

Moreover, in Embodiments 1, 2, and 3, as shown in FIG. 2 or 6, the marks 110F and 110B are offset from the center of the disc and are disposed in parallel with the reading portion of the analysis target B. In this case, a distance between the mark and a sample is not so different between the inner edge and the outer edge of the disc. Thus, when a relatively large sample (several millimeters or more) is visualized, a distortion is small in the reproduction of an image.

Embodiment 4

In the analysis discs 108 of the foregoing embodiments, the mark 110F, the mark 110F and the mark 110B, and the mark 110B are all formed by printing as shown in FIG. 5(a). As shown in FIG. 5(b), the mark 110F, the mark 110F and the mark 110B, and the mark 110B can be similarly formed by providing a portion 118, which has lost a mirror surface, on a part of the track 101a having been subjected to mirror-like finishing. To be specific, BCA is provided on a mirror surface of a DVD.

Further, as shown in FIG. 5(c), the mark 110F, the mark 110F and the mark 110B, and the mark 110B can be similarly formed by providing an oddly shaped portion 119 such as a concave portion on a part of the outside of the analysis disc 108. To be specific, the disc is changed in shape to reflect light on a data track surface.

The specific positions and ranges of the portion 118, which has lost a mirror surface, and the oddly shaped portion 119 on the analysis disc 108 correspond to one of a position immediately in front of, a position in the front of or behind, and a position just behind the reading area 109 in the rotating direction, the reading area having the analysis object B therein. The positions and ranges are similar to those of the marks in the foregoing embodiments.

An analysis apparatus, which uses the analysis disc 108 having the portion 118 having lost a mirror surface or the oddly shaped portion 119, is different from the foregoing embodiments only in that the portion 118 having lost a mirror surface or the oddly shaped portion 119 are read and trigger signals having detected mark positions are generated.

In FIGS. 5(b) and 5(c), the position of the analysis object B on the analysis disc 108 is the same as that of FIG. 5(a).

Embodiment 5

In the foregoing embodiments, the mark 110F, the mark 110F and the mark 110B, and the mark 110B are formed by printing, removing a mirror surface, or forming an odd shape. The mark may be provided on the pit, the groove 112a, or the land 112b of the analysis disc 108.

To be specific, by detecting the mark with a pickup 103, it is possible to make a distinction between a track data portion and a reading area 109 having an analysis object B therein. An example will be discussed below.

The mark is constituted of pits such as EFM and MFF. To be specific, the mark is constituted of prepits, LPP (land prepits) (recorded as address information on a DVD-R/RW and engraved as prepits on lands between tracks, and to be specific, CAPA (prepits for the address on a DVD-RAM)) and so on. Modulation of some kind including a wobble is superimposed on a groove or a land.

The specific position and range of the mark constituted of pits, grooves, or lands on the analysis disc 108 correspond to one of a position immediately in front of, a position in the front of or behind, or a position just behind the reading area 109 in the rotating direction, the reading area 109 having the analysis object B therein. The position and range are similar to those of the marks in the foregoing embodiments.

An analysis apparatus, which uses the analysis disc 108 having the mark constituted of pits, grooves, or lands, is different from the foregoing embodiments only in that the mark is read by the pickup 103 and trigger signals having detected mark positions are generated.

On the analysis disc 108 where the mark is constituted of pits, groove, or lands, the specific pattern of the mark is varied by modulating the mark so that the array position or analysis contents of the analysis object B can be identified on the analysis disc 108. In this case, the analysis apparatus using the analysis disc 108 is configured as below.

The reproducing device 107 of the analysis apparatus using the analysis disc 108 where the specific pattern of the mark is varied by performing modulation identifying the array position of the analysis object B, the reproducing device 107 being configured so as to output image data on which the pickup 103 reads the mark and time base correction is performed relative to trigger signals having detected mark positions, and data for identifying, based on the specific pattern of the read mark, the array position where the image data belongs to the analysis object B on the analysis disc 108.

Figure 7:
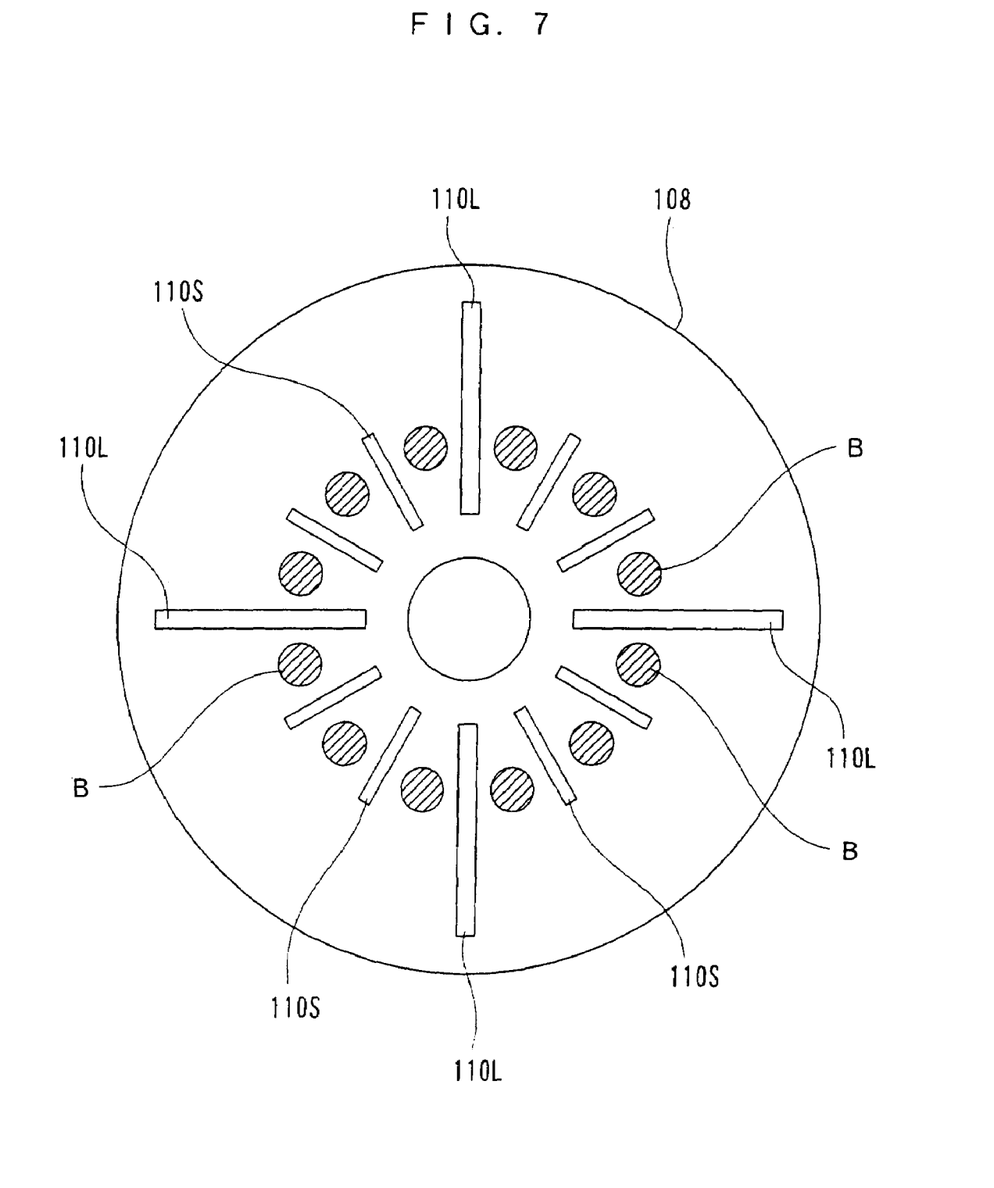
FIG. 7 is a plan view showing an analysis disc according to Embodiment 5 of the present invention.

For example, when the analysis disc shown in FIG. 7 is configured using such an analysis apparatus, it is possible to conduct blood tests on two or more persons at the same time and manage test results for each person.

The illustrated analysis disc 108 is divided broadly into four regions by marks 110L, and three analysis objects B can be disposed in respective regions with marks 110S. The marks 110L and 110S are formed so as to radially stretch from the center of the disc along the radial direction with different patterns, so that the analysis objects B can be managed.

With this configuration, blood from a different person is spotted in each region, and then, tests are conducted. Thus, it is possible to manage the test results of four persons at the same time. Further, on this disc, three analysis objects B can be disposed for each person, so that the same test can be repeated three times for each person.

In the reproducing device 107 of the analysis apparatus using the analysis disc 108 where the specific pattern of the mark is varied by performing modulation identifying the analysis contents of the analysis object B, the reproducing device 107 being configured so as to manage image data on which the pickup 103 reads the mark and time base correction is performed relative to trigger signals having detected mark positions, and manage the kind of desired analysis object in a coordinated manner based on the specific pattern of the read mark. Thereafter, the contents of image processing, the counting method, the decision method, and so on are automatically processed according to the kind of analysis object.

"The kind of analyst object" indicates analysis items such as cholesterol, erythrocyte, and leukocyte when a sample is blood. Further, the reproducing device 107 serving as an image processor is configured as follows: regarding reading signals of the mark, visualization is performed to align time axes relative to the position of the mark, an image of the analysis object is obtained or shape count is performed, and the visualization results are managed in association with the reading area based on the specific pattern.

A disc shown in FIG. 7 can be used as an analysis disc applicable to such an analysis apparatus. In this case, the kind of analysis object is changed in each region of the analysis disc, so that blood of one person can be tested and managed three times for four kinds of test items. Moreover, the kind of analysis object can be changed in a region of the analysis disc. In this case, blood of two or more persons can be tested and managed for two or more test items on a single disc.

Figure 8:
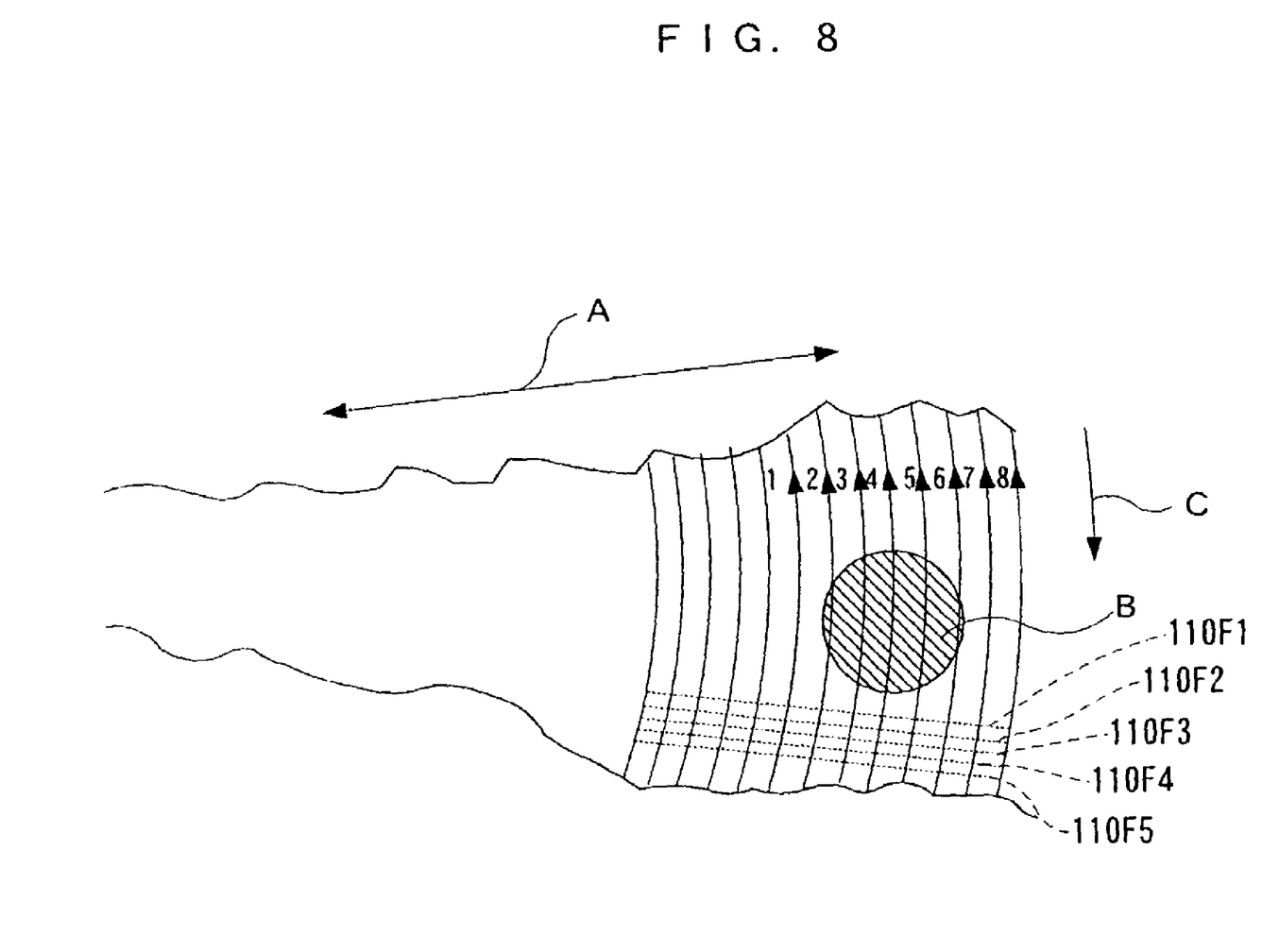
FIG. 8 is an enlarged sectional view of the analysis disc that shows the formation of a mark according to Embodiment 5 of the present invention.

The mark 110F, the mark 110F and the mark 110B, and the mark 110B may be provided as two or more marks in consideration of the occurrence of a reading error. For example, the order of marks from the closest to the analysis object B is modulated and recorded on a marker, and then the order is read, so that the function of the marker can be performed by interpolation even in the event of a reading error of the marker.

To be specific, as shown in FIG. 8, in the case where the mark 110F has marks 110F5, 110F4, . . . , and 110F1 at regular intervals of "5", "4", "3", "2", and "1" as the mark 110F comes closer to the analysis object B, for example, even when the mark 110F2 of "2" is not read and missed, previously read "5", "4", and "3" are counted and the rule of intervals is understood, so that "2" can be generated without any trouble. Also when "1" is missed, "0" position is similarly expected and thus the function of a video acquisition trigger can be performed.

With this interpolation, in CAV control where an optical disc has a constant rotation instead of CLV control having a constant linear velocity, the acquisition of the rule of mark intervals is used in synchronization with video processing, so that an image can be acquired.

That is, by using the mark intervals as in the CAV reading of an ordinary CD and DVD, CAV control reading is performed on an image of a sample. In the case of CAV control, control is performed so that a disc has a constant rotation. Therefore, a travel distance is different between the inner edge and the outer edge for each hour. When an image of a sample is acquired, acquisition at regular intervals results in an image different from actual one. In order to eliminate this problem, it is necessary to have different intervals of video acquisition between the inner edge and the outer edge. It is strictly necessary to have the same conditions as the video acquisition of CLV control. In this method, the mark intervals of the marker are provided regularly on the disc regardless of whether on the inner edge or the outer edge. A reading device synchronizes a reading cycle of an image with the mark intervals and acquires an image of a sample while keeping the synchronization. In this case, the method is used for a unit which changes the reading cycle according to a change in linear velocity of the disc.

Although the foregoing embodiments discussed a blood sample, the present invention is applicable to other kinds of analysis. To be specific, the present invention is applicable to analysis on drinking water such as tap water and analysis on water quality of a reservoir and so on.

In each of the foregoing embodiments, as shown in FIG. 5, the track 101a is provided above or below the analysis object B. The present invention can be implemented without providing the track 101a in the region of the analysis object B.

As described in Embodiments 1 to 5, according to the analysis apparatus of the present invention and the analysis disc used for the same, an analysis disc is used where a mark is recorded over the radial direction of a reading area, in which an analysis object is disposed, at least in front of or behind the reading area in the rotation direction, a pickup is provided which detects the mark and detection light from the analysis object disposed on the set analysis disc, and an image processor which performs video acquisition or shape count on the analysis object by performing video processing for aligning time axes relative to the position of the mark, on the analysis object and the reading signals of the mark, the analysis object being read in time series by the pickup which traces tracks. Thus, analysis accuracy can be expected to improve from the conventional art.

The invention claimed is:

1. An analysis disc (108) for reproducing and tracing on a pit or a groove and has a data region for controlling rotation of the disc and a reading area having an analysis object therein, wherein a mark (110) is recorded over a radial direction of the reading area (109) disposed with the analysis object, at least in one of frontward and rearward positions of the reading area in a rotation direction.

2. The analysis disc according to claim 1, wherein the mark (110) is formed as a pit (112a), a groove (112a), or a land (112b), or by printing (111), removing a mirror surface (118), or forming an odd shape (119).

3. The analysis disc according to claim 1, wherein the mark (110) is formed as a pit (112a), a groove (112a), or a land (112b) with a specific pattern different from the data region.

4. The analysis disc according to claim 3, wherein the specific pattern of the mark (110) is varied according to a plurality of reading areas (109) each being disposed with the analysis object.

5. The analysis disc according to claim 3, wherein the specific pattern of the mark (110) is varied according to a kind of the analysis object disposed in the reading area (109).

* * * * *